| United States Patent [19] | [11] 3,948,979 |
|---|---|
| Patterson | [45] Apr. 6, 1976 |

[54] PROCESS FOR SYNTHESIS OF CRYSTALLINE 2-METHACRYLOYLOXYETHYLTRIME-THYLAMMONIUM CHLORIDE

[75] Inventor: Kendall W. Patterson, Newark, Del.

[73] Assignee: Hercules Incorporated, Wilmington, Del.

[22] Filed: July 3, 1974

[21] Appl. No.: 485,471

[52] U.S. Cl............................................. 260/486 R
[51] Int. Cl.²....................................... C07C 69/54
[58] Field of Search........................ 260/486, 486 R

[56] References Cited
UNITED STATES PATENTS

| 2,729,622 | 1/1956 | Albisetti et al. | 260/486 |
|---|---|---|---|
| 2,744,130 | 5/1956 | Winberg | 260/486 |
| 3,766,156 | 10/1973 | Kine et al. | 260/486 |
| 3,780,092 | 12/1973 | Samour et al. | 260/486 |

Primary Examiner—Lorraine A. Weinberger
Assistant Examiner—P. J. Killos
Attorney, Agent, or Firm—Michael B. Keehan

[57] ABSTRACT

A process for preparation of 2-methacryloyloxyethyl-trimethylammonium chloride crystals in high yields from dimethylaminoethyl methacrylate and methyl chloride is provided. Reaction takes place in an organic reaction solvent. The product crystals formed are washed with a washing liquid which is a nonsolvent for the product crystals but which is a solvent for the reaction solvent, reactants and impurities therein. The product crystals are 2-methacryloyloxyethyltrimethylammonium chloride monomers which can be polymerized or copolymerized with other vinyl monomers to prepare flocculants.

10 Claims, No Drawings

PROCESS FOR SYNTHESIS OF CRYSTALLINE 2-METHACRYLOYLOXYETHYLTRIMETHYLAMMONIUM CHLORIDE

This invention relates to a process for the synthesis of crystalline 2-methacryloyloxyethyltrimethylammonium chloride.

2-methacryloyloxyethyltrimethylammonium chloride is the quaternary ammonium salt of dimethylaminoethyl methacrylate and methyl chloride. The process for preparation of the methyl sulfate analog of this monomer, i.e., 2-methacryloyloxyethyltrimethylammonium sulfate is well known. In this process dimethylaminoethyl methacrylate is reacted with dimethyl sulfate in aqueous solution, generally comprising about 50% by weight of the dimethylaminoethyl methacrylate. Manufacture of 2-methacryloyloxyethyltrimethylammonium chloride monomer from dimethylaminoethyl methacrylate and methyl chloride in the form of an aqueous solution has not been found to be satisfactory. Deleterious impurities present in dimethylaminoethyl methacrylate and methyl chloride remain with the aqueous solution of monomer reaction product and are extremely difficult to remove from the monomer. Hydrolysis of dimethylaminoethyl methacrylate and methyl chloride also occurs in aqueous solution reducing the yields of 2-methacryloyloxyethyltrimethylammonium chloride.

In accordance with this invention, 2-methacryloyloxyethyltrimethylammonium chloride is prepared in crystalline form in high yields by a process comprising the following steps:

a. forming a solution of dimethylaminoethyl methacrylate in an organic reaction solvent therefor,
b. admixing methyl chloride to the dimethylaminoethyl methacrylate solution in at least a substantially stoichiometric amount,
c. agitating the admixture of step (b) and maintaining the temperature of the admixture at from about 25°C. to about 70°C. thereby producing a slurry having a dispersed phase comprising 2-methacryloyloxyethyltrimethylammonium chloride crystals and a continuous phase comprising reaction solvents and unreacted dimethylaminoethyl methacrylate and methylchloride,
d. washing said 2-methacryloyloxyethyltrimethylammonium chloride crystals with an organic washing liquid which is a nonsolvent for said crystals and which is a solvent for both dimethylaminoethyl methacrylate and the reaction solvent, and
e. recovering purified 2-methacryloyloxyethyltrimethylammonium chloride crystals.

The following examples more fully illustrate the process of this invention. In the examples, parts and percentages are by weight unless otherwise specified.

EXAMPLE 1

About 1000 parts of acetone is charged to a reactor vessel equipped with an agitator. To the acetone in the reactor is added about 300 parts of dimethylaminoethyl methacrylate. The dimethylaminoethyl methacrylate is inhibited with about 2000 ppm of the methyl ether of hydroquinone. This mixture is agitated and heated to about 50°C. Methyl chloride gas is then metered to the reactor so that a stoichiometric quantity of methyl chloride is added to the reactor over a period of slightly less than one hour. At the end of one hour, the reaction vessel pressure is about 40 psig. The reaction is exothermic. Cooling is employed to maintain the temperature in the reactor at about 70°C. Agitation is maintained continuously, and after about four hours total reaction time, unreacted gaseous methyl chloride is vented from the reactor. The resulting slurry mixture comprising a dispersed phase comprising 2-methacryloyloxyethyltrimethylammonium chloride crystals and a continuous phase comprising acetone is pumped from the reactor to a storage vessel in which the 2-methacryloyloxyethyltrimethylammonium chloride crystals rapidly settle from the slurry. Acetone is syphoned from the separated crystals. The methacryloyloxyethyltrimethylammonium chloride crystals are mixed with 4 parts of acetone to form a mixture comprising 20% by weight of methacryloyloxyethyltrimethylammonium chloride crystals. This mixture is agitated forming a slurry of methacryloyloxyethyltrimethylammonium chloride crystals dispersed in acetone. This dispersion is maintained for about 15 minutes. The acetone is then separated from the crystals by syphoning. This washing step is repeated two additional times. The purified 2-methacryloyloxyethyltrimethylammonium chloride crystals are analyzed as follows:

| | |
|---|---|
| % Assay | 99.8 |
| % Total Volatiles | 0.2 |
| % DMAEMA | 0 |
| % Polymer in Monomer | 0 |
| Inhibitor (ppm) | 8 |

EXAMPLE 2

Example 1 is repeated with the exception that toluene is employed as both the reaction solvent and purification solvent in place of acetone. The 2-methacryloyloxyethyltrimethylammonium chloride crystals are analyzed as follows:

| | |
|---|---|
| % Assay | 98.9 |
| % Total Volatiles | 0.3 |
| % Excess DMAEMA | 0 |
| % Polymer in Monomer | 0.8 |
| Inhibitor (ppm) | 5 |

EXAMPLES 3–9

The following examples illustrate the effect of reaction time, mole ratio of reactants and reaction temperature on the yield of 2-methacryloyloxyethyltrimethylammonium chloride. In these examples acetone is employed as the reaction solvent and the processing procedures employed follow the procedure of Example 1. The results of these examples are set forth in Table 1.

TABLE 1

| Ex. | Methyl Chloride DMAEMA[1] (Mole Ratio) | Reaction Time (Hrs.) | Reaction Temp. (°C.) | Yield MTMAC[2] (Wt.%) |
|---|---|---|---|---|
| 3 | 1.0 | 2.0 | 60 | 73 |
| 4 | 1.0 | 3.0 | 60 | 81 |
| 5 | 1.0 | 4.0 | 60 | 85 |
| 6 | 1.0 | 2.0 | 70 | 83 |
| 7 | 1.0 | 3.0 | 70 | 88 |
| 8 | 1.0 | 4.0 | 70 | 91 |

TABLE 1-continued

| Ex. | Methyl Chloride DMAEMA[1] (Mole Ratio) | Reaction Time (Hrs.) | Reaction Temp. (°C.) | Yield MTMAC[2] (Wt.%) |
|---|---|---|---|---|
| 9 | 2.0 | 4.0 | 70 | 100 |

[1]dimethylaminoethyl methacrylate
[2]2-methacryloyloxyethyltrimethylammonium chloride In conducting the process of this invention, any organic liquid which is a solvent for dimethylaminoethyl methacrylate and which is a nonsolvent for 2-methacryloyloxyethyltrimethylammonium chloride can be employed as the reaction solvent. Illustrative reaction solvents include ketones such as acetone, methyl ethyl ketone, methyl n-propyl ketone, diethyl ketone, di-n-propyl ketone, and the like; aliphatic hydrocarbons such as hexane, heptane, octane, nonane and the like; and aromatics such as toluene, benzene, ethyl benzene, isopropyl benzene, dimethylbenzenes (xylenes) and the like.

The dimethylaminoethyl methacrylate employed in the process of this invention must be inhibited with a polymerization inhibitor soluble in DMAEMA and capable of reducing the reactivity of the double bond in DMAEMA. Illustrative polymerization inhibitors for DMAEMA include the methyl ether of hydroquinone, hydroquinone, quinone and phenothiazine.

In the process of this invention methyl chloride is added to the solution of DMAEMA in at least stoichiometric amounts. Methyl chloride can be employed either as a gas or a liquid. The process can be performed on either a batch or continuous basis.

Reaction time required to achieve substantially complete reaction of methyl chloride with dimethylaminoethyltrimethylammonium chloride will vary principally with reaction temperature and mole ratio of reactants, the reaction proceeding faster at higher temperatures and with a greater than stoichiometric amount of methyl chloride present. The process of this invention is conducted at temperatures of from about 25°C. to about 70°C. and preferably at temperatures of from about 50°C. to about 70°C. When operating at lower temperatures of say 25°C., a greater than stoichiometric amount of methyl chloride must be employed in order to achieve a reasonable reaction rate. Above a temperature of about 70°C. the reaction product, i.e., 2-methacryloyloxyethyltrimethylammonium chloride monomer will start to polymerize resulting in reduced yields and a product of decreased purity.

In the process of this invention, the 2-methacryloyloxyethyltrimethylammonium chloride is prepared in crystalline form and therefore the monomer crystals can be purified by either slurrying said crystals in a washing liquid or displacement washing of said crystals, employing as washing liquid, a solvent for the reaction solvent which is also a nonsolvent for the 2-methacryloyloxyeithytrimethylammonium chloride crystals. It is preferable to employ as the washing liquid, the same solvent as the reaction solvent employed in the process for the preparation of the crystals. Thus, any of the reaction solvents heretofore described can be employed as the washing liquid in the process of this invention as long as they meet the solubility requirements described for both reaction solvents and product crystals.

In a typical washing procedure, the reaction mass comprising 2-methacryloyloxyethyltrimethyl ammonium chloride crystals, any unreacted dimethylaminoethyl methacrylate and reaction solvent are diluted with sufficient washing liquid to form an admixture comprising about 20% by weight of solids. The admixture is agitated to form a slurry having a dispersed phase comprising 2-methacryloyloxyethyltrimethylammonium chloride crystals and a continuous phase comprising reaction solvent, washing liquid, and any unreacted dimethylaminoethyl methacrylate. The slurry is maintained for time sufficient for a substantial proportion of impurities in the 2-methacryloyloxyethyltrimethylammonium chloride to be extracted into the washing liquid. The agitation is stopped and the washing liquid is separated from the product crystals by a suitable means such as centrifugation or filtration. The product crystals are reslurried with additional washing liquid and the washing step heretofore described is repeated. The number of washes, the amounts of washing liquid employed in each wash, and the length of time during which the product crystals are dispersed in the washing liquid may be varied to achieve effective removal of impurities through use of simple experimentation.

Variations of the washing methods described for removal of impurities from 2-methacryloyloxyethyltrimethylammonium chloride crystals can be employed. Thus, the product crystals can be separated from unreacted dimethylaminoethyl methacrylate in reaction solvent by vacuum or pressure filtration and subsequently rinsed with a washing liquid until a product of high purity is recovered.

In the process of this invention it is desirable to obtain 2-methacryloyloxyethyltrimethylammonium chloride of high purity for subsequent polymerization. It is therefore preferable to remove as completely as possible all of the polymerization inhibitor present in the 2-methacryloyloxyethyltrimethylammonium chloride crystals in order that this monomer can be polymerized or copolymerized as the case may be. The presence of the inhibitor in the 2-methacryloyloxyethyltrimethylammonium chloride crystals can prevent effective polymerization of the monomer.

The effect of slurry washing of the 2-methacryloyloxyethyltrimethylammonium chloride crystals on removal of inhibitor in the product crystals is illustrated by the data set forth in Table 2 below.

Table 2

| Inhibitor Removal by Slurry Washing | |
|---|---|
| No. of Slurry Washes[a] | MEHQ[b] in MTMAC (ppm) |
| 0[c] | 145 |
| 1 | 28 |
| 3 | 8 |

[a]Solvent added in amount sufficient to form a slurry containing 20% total solids.
[b]Methyl ether of hydroquinone (polymerization inhibitor)
[c]Reaction solvent removed with no further purification.

Following washing of the 2-methacryloyloxyethyltrimethylammonium chloride crystals, the crystals can be dried. Drying is preferably done under vacuum at a temperature of about 50°C. to about 60°C. Storage stability of the crystals is good. 2-methacryloyloxyethyltrimethylammonium chloride monomer can be polymerized to form homopolymers or can be copolymerized with other vinyl monomers such as acrylamide to produce products which are highly efficient flocculants and coagulant aids for industrial and municipal liquid-solids separation process.

What I claim and desire to protect by Letters Patent is:

1. A process for manufacture of 2-methacryloyloxyethyltrimethylammonium chloride comprising
   a. forming a solution of dimethylaminoethyl methacrylate in an organic reaction to solvent therefor,
   b. admixing methyl chloride to the solution of dimethylaminoethyl methacrylate in at least a substantially stoichiometric amount,
   c. agitating the admixture of step (b) and maintaining the temperature of the admixture from about 25°C. to about 70°C., thereby producing a slurry having a dispersed phase comprising 2-methacryloyloxyethyltrimethylammonium chloride crystals and a continuous phase comprising reaction solvent and unreacted dimethylaminoethyl methacrylate and methyl chloride,
   d. washing the 2-methacryloyloxyethyltrimethylammonium chloride crystals with an organic washing liquid which is a nonsolvent for said crystals and which is a solvent for both dimethylaminoethyl methacrylate and the reaction solvent,, and
   e. recovering 2-methacryloyloxyethyltrimethylammonium chloride.

2. The process of claim 1 in which the reaction solvent comprises acetone.

3. The process of claim 2 in which the washing liquid comprises acetone.

4. The process of claim 1 in which the reaction solvent comprises toluene.

5. The process of claim 4 in which the washing liquid comprises toluene.

6. The process of claim 1 in which the reaction temperature is maintained at from about 50° to about 70°C.

7. A process for manufacture of 2-methacryloyloxyethyltrimethylammonium chloride comprising
   a. forming a solution of dimethylaminoethyl methacrylate in an organic reaction solvent therefor,
   b. admixing methyl chloride to the the solution of dimethylaminoethyl methacrylate in at least a substantially stoichiometric amount,
   c. agitating the admixture of step (b) and maintaining the temperature of the admixture at between about 50°C. and about 70°C., thereby producing a slurry having a dispersed phase comprising 2-methacryloyloxyethyltrimethylammonium chloride crystals and a continuous phase comprising reaction solvent and unreacted dimethylaminoethyl methacrylate and methyl chloride,
   d. separating the 2-methacryloyloxyethyltrimethylammonium chloride crystals from the continuous phase,
   e. admixing the 2-methacryloyloxyethyltrimethyl ammonium chloride crystals and a washing liquid and agitating said admixture to form a slurry having a dispersed phase comprising said crystals and a continuous phase comprising washing liquid, and
   f. separating purified 2-methacryloyloxyethyltrimethylammonium chloride crystals from the admixture of step (e).

8. The process of claim 7 in which the reaction solvent comprises acetone.

9. The process of claim 8 in which the washing liquid comprises acetone.

10. The process of claim 7 in which the reaction temperature is maintained at between about 50°C. and 70°C.

* * * * *